(12) United States Patent
Richardson et al.

(10) Patent No.: US 8,398,718 B2
(45) Date of Patent: Mar. 19, 2013

(54) ACETABULAR CUP WITH ROTATABLE BEARING MEMBER

(75) Inventors: Rodney Ian Walter Richardson, Melbourne (AU); Kevin M. Mihelc, Hoboken, NJ (US)

(73) Assignee: Rodney Ian Walter Richardson, Melbourne (AU)

( * ) Notice: Subject to any disclaimer, the term of this patent is extended or adjusted under 35 U.S.C. 154(b) by 0 days.

(21) Appl. No.: 13/028,598

(22) Filed: Feb. 16, 2011

(65) Prior Publication Data

US 2012/0209398 A1 Aug. 16, 2012

(51) Int. Cl.
*A61F 2/32* (2006.01)
(52) U.S. Cl. ............. 623/22.17; 623/22.11; 623/22.25
(58) Field of Classification Search ....... 623/22.1–22.18, 623/22.21–22.325; A61F 2/32
See application file for complete search history.

(56) References Cited

U.S. PATENT DOCUMENTS

| | | |
|---|---|---|
| 3,694,821 A | 10/1972 | Moritz |
| 3,868,730 A | 3/1975 | Kaufer et al. |
| 3,886,601 A | 6/1975 | Findlay |
| 4,623,351 A | 11/1986 | Church |
| 4,798,610 A | 1/1989 | Averill et al. |
| 4,960,427 A | 10/1990 | Noiles |
| 5,641,323 A | 6/1997 | Caldarise |
| 5,782,923 A | 7/1998 | Engelbrecht et al. |
| 6,093,208 A | 7/2000 | Tian |
| 6,129,765 A | 10/2000 | Lopez et al. |
| 6,136,033 A | 10/2000 | Suemer |
| 6,152,961 A | 11/2000 | Ostiguy, Jr. et al. |
| 6,162,256 A | 12/2000 | Ostiguy, Jr. et al. |
| RE38,409 E | 1/2004 | Noiles |
| 6,802,866 B2 | 10/2004 | Bunz |
| 6,916,342 B2 | 7/2005 | Frederick et al. |
| 7,108,720 B2 | 9/2006 | Hanes |
| 7,153,328 B2 | 12/2006 | Kim |
| 7,179,296 B2 | 2/2007 | Dooney |
| 7,179,297 B2 | 2/2007 | McLean |

(Continued)

FOREIGN PATENT DOCUMENTS

| | | |
|---|---|---|
| DE | 4401815 A1 | 8/1994 |
| EP | 1952786 A2 | 8/2008 |

(Continued)

OTHER PUBLICATIONS

Extended European Search Report for application 12155108.9 dated May 22, 2012.

(Continued)

*Primary Examiner* — Thomas J Sweet
*Assistant Examiner* — Jason-Dennis Stewart
(74) *Attorney, Agent, or Firm* — Lowe Hauptman Ham & Berner, LLP

(57) ABSTRACT

A prosthetic hip implant system includes a prosthetic femoral component having a stem portion, a neck portion coupled to the stem portion and a part-spherical head coupled to the neck portion. An acetabular component is provided which has a housing, the housing having a part-spherical inner surface having an open end with a circumferential rim portion. The rim portion has a circumferential radially inwardly extending flange. A bearing element is mounted within the housing and has a part-spherical first outer surface region engaging the part-spherical inner surface of the housing. The part-spherical first outer surface region extends at a first radius from a center. The bearing element has a second part-spherical outer surface region extending a distance from the center less than the first radius to form a stop surface for contacting the rim.

20 Claims, 6 Drawing Sheets

U.S. PATENT DOCUMENTS

| | | |
|---|---|---|
| 7,294,150 B1 | 11/2007 | Mandell et al. |
| 7,335,231 B2 | 2/2008 | McLean |
| 7,455,694 B2 | 11/2008 | Epaules et al. |
| 7,520,902 B2 | 4/2009 | Deloge et al. |
| 7,572,294 B2 | 8/2009 | Meridew et al. |
| 2003/0171817 A1 | 9/2003 | Rambert et al. |
| 2003/0187512 A1 | 10/2003 | Frederick et al. |
| 2003/0212458 A1 | 11/2003 | Harris et al. |
| 2004/0143341 A1 | 7/2004 | McLean |
| 2004/0193282 A1 | 9/2004 | Hanes |
| 2005/0021148 A1 | 1/2005 | Gibbs |
| 2005/0288793 A1 | 12/2005 | Dong et al. |
| 2008/0140215 A1 | 6/2008 | Gladdish et al. |
| 2009/0088864 A1 | 4/2009 | Lewis et al. |
| 2009/0171464 A1 | 7/2009 | Imhof |
| 2009/0192626 A1 | 7/2009 | Keefer et al. |
| 2009/0289806 A1 | 11/2009 | Thornberry |
| 2010/0161072 A1 | 6/2010 | Drescher |

FOREIGN PATENT DOCUMENTS

| | | |
|---|---|---|
| FR | 2785525 A1 | 5/2000 |
| WO | 2009118673 A1 | 10/2009 |

OTHER PUBLICATIONS

Extended European Search Report for application 12155109.7 dated Jun. 1, 2012.

ACETABULAR CUP WITH ROTATABLE BEARING MEMBER

BACKGROUND OF THE INVENTION

This invention relates to a prosthetic hip implant system which comprises a part-spherical cup adapted for location in an acetabulum and having a part-spherical inner bearing surface to receive a part-spherical ball head which can be attached to a prosthetic stem for location in a femur and in which the inner bearing surface of the cup extends around an angle of more than 180°. Cups of this type are known which comprise a single bearing element made, for example, of a synthetic plastic material such as ultra high molecular weight polyethylene or metal. The inner bearing surface can also be formed on an insert which again can be of a synthetic plastic material, a ceramic, or a metal and which is carried in an outer housing, the outer housing engages the acetabulum with which it is to be used and being held in place by, for example, cement or by mechanical means, for example nails or screws. The cup is used in connection with Total Hip Arthroplasty which includes implanting a femoral component in the femur which component normally includes a stem, a neck and ball head.

In other known constructions of the cup the inner bearing surface can be provided on an inner liner or insert made from a different material from an outer backing which engages the acetabulum. Dual mobility cups or bipolar cups generally comprise an inner bearing which receives the part-spherical ball head and which inner bearing itself is freely rotatably mounted in a part-spherical housing which has an outer surface for engaging an acetabulum and an inner bearing surface. The bearing outer surface engages the inner bearing surface of the outer housing which engages the acetabulum. This type of cup allows greater mobility of angular movement. Such cups are shown in U.S. Pat. No. 4,798,610 and U.S. Publication 2004/0143341.

In all these constructions, and, more especially, dual mobility cups, it is advantageous to have a means for retaining the ball head against the inner bearing surface. There are several ways of retaining the ball head inside the inner bearing surface. For example, U.S. Pat. No. 4,798,610 uses a ring seated on a conically tapered surface in the inner bearing. The second arrangement can consist of having two flats on the head and turning the head at 90° prior to inserting it into the cup and then again turning the head back through 90°. A disadvantage with this type of construction is that specific heads are required and there is the risk of wear due to the truncating of the head. A system of this type is shown in FR 2 785 525 and U.S. Patent Publication No. 20030171817.

Another way for retaining the ball in a part-spherical cup adapted for location in an acetabulum having a part-spherical inner bearing surface to receive the part-spherical ball head which can be attached to a stem for location in a femur is by using flat surfaces on the cup and ball. The part-spherical inner bearing surface of the cup extends around an angle of more than 180°, and a portion thereof adjacent an entry mouth is formed with a substantially flat face which is at a radius from the center of the part-spherical inner bearing surface. This radius is less than the radius of the remainder of the cup, and the ball head has a co-operating substantially flat face on its part-spherical surface on which is provided a structure to receive and retain the stem with which it is to be used, and which prior to attachment to the stem allows it to be located in the cup and rotated so that it is retained thereon. The dimensions and configuration of the part-spherical inner bearing surface and the part-spherical bearing surface on the ball head being arranged to cause a movement of translation of the head during rotation to displace the head so that there is a crescent shaped retention area on each opposed side.

Such a construction is shown in U.S. Pat. No. 7,520,902. An advantage of this construction is that standard sized ball heads can be used. The entry into the cup can be closely controlled by the dimensions of the flat on the inner bearing surface so that the operation of the ball head against the bearing surface is accurate.

In a preferred construction the transverse axis of the mouth of the cup which is substantially parallel with the flat face of the ball head when being inserted is offset from the transverse axis of the inner bearing surface of the cup. The offset can be less than 10 mm, for example up to 5 mm.

The invention can be applied to cups and balls of any suitable material, for example synthetic plastics material, metals or ceramics. An amount, for example, 1 mm of free subluxation can be incorporated if necessary.

BRIEF SUMMARY OF THE INVENTION

The present invention can be applied to cups in which the inner bearing surface is provided on an inner bearing element or to dual mobility or bi-polar cups in which the inner bearing element is formed as an insert which can move within another bearing surface within a backing and to cemented or non-cemented cups. The prosthetic hip implant system of the present invention comprises a prosthetic femoral component having a stem portion, a neck portion coupled to the stem portion and a part-spherical head coupled to the neck portion. An acetabular component is provided which has a housing, the housing having a part-spherical inner bearing surface having an open end with a circumferential rim portion, the rim portion has a circumferential radially inwardly extending ramp or inwardly tapered area. The bearing element is received within the housing and has a part-spherical first outer surface bearing region engaging the part-spherical inner bearing surface of the housing. The bearing element has a part-spherical inner bearing surface region having an open end for receiving the head mounted on the neck of the femoral component. The part-spherical first outer surface region of the bearing element extends about central axis of the inner surface open end. The central axis intersects a pole of and a center of rotation of the part-spherical first outer surface bearing region of the bearing element. The bearing element has a second part-spherical outer surface region extending from adjacent the open end towards the pole. The first outer surface region extending radially further from a center of the part-spherical inner surface of the bearing element than the second part-spherical surface region. The bearing element center point may be the center of rotation of the first and second part-spherical outer surface regions as well as the part-spherical inner surface region. This center point lies along the polar axis.

The bearing element part-spherical first outer surface region extends from the pole towards the open end to define a circumferentially extending contact surface extending in an inwardly tapered direction between the part-spherical first surface and the second outer surface. The circumferential contact surface preferably extends 360 degrees around the part-spherical first outer surface and the second part-spherical outer surface. The circumferential contact surface could be broken into two or more segments separated by gaps. The circumferential contact surface is located on the bearing element intermediate the pole and an equator which extends through the center of rotation of the part-spherical first outer surface perpendicular to the polar axis. The contact surface could be at a shallow angle to the polar axis of the inner bearing surface and at a shallow angle to the central axis of the first part-spherical outer surface. The circumferential contact surface is located at the position intermediate the pole and the equator such that upon rotation of the bearing element with respect to the housing the neck of the femoral component contacts the bearing element open end prior to the inwardly extending circumferential rim portion of the housing. The inwardly extending circumferential ramp or tapered area of the rim has an inner diameter less than an outer diameter of the first part-spherical outer surface portion of the bearing element and less than an outer diameter of the bearing element at an equator of the second part-spherical outer surface portion to produce a slight interference upon insertion of the bearing element into the housing. The tapered or ramped surface of the rim facing the polar area of the housing has an angled surface matching the contact surface on the bearing element. The outer diameter of the first part-spherical outer surface portions at the circumferential contact surface is inwardly deformable upon contact with the rim to a diameter less than the inner diameter of the inwardly extending flange portion of the housing or shell. The circumferential contact surface may extend around a latitude of about 40° to 45° from the equator. The housing and/or shell may be mounted within a shell contacting an acetabulum. The housing may be metal and cemented into the acetabulum or attached thereto by screws.

BRIEF DESCRIPTION

Figure 1:
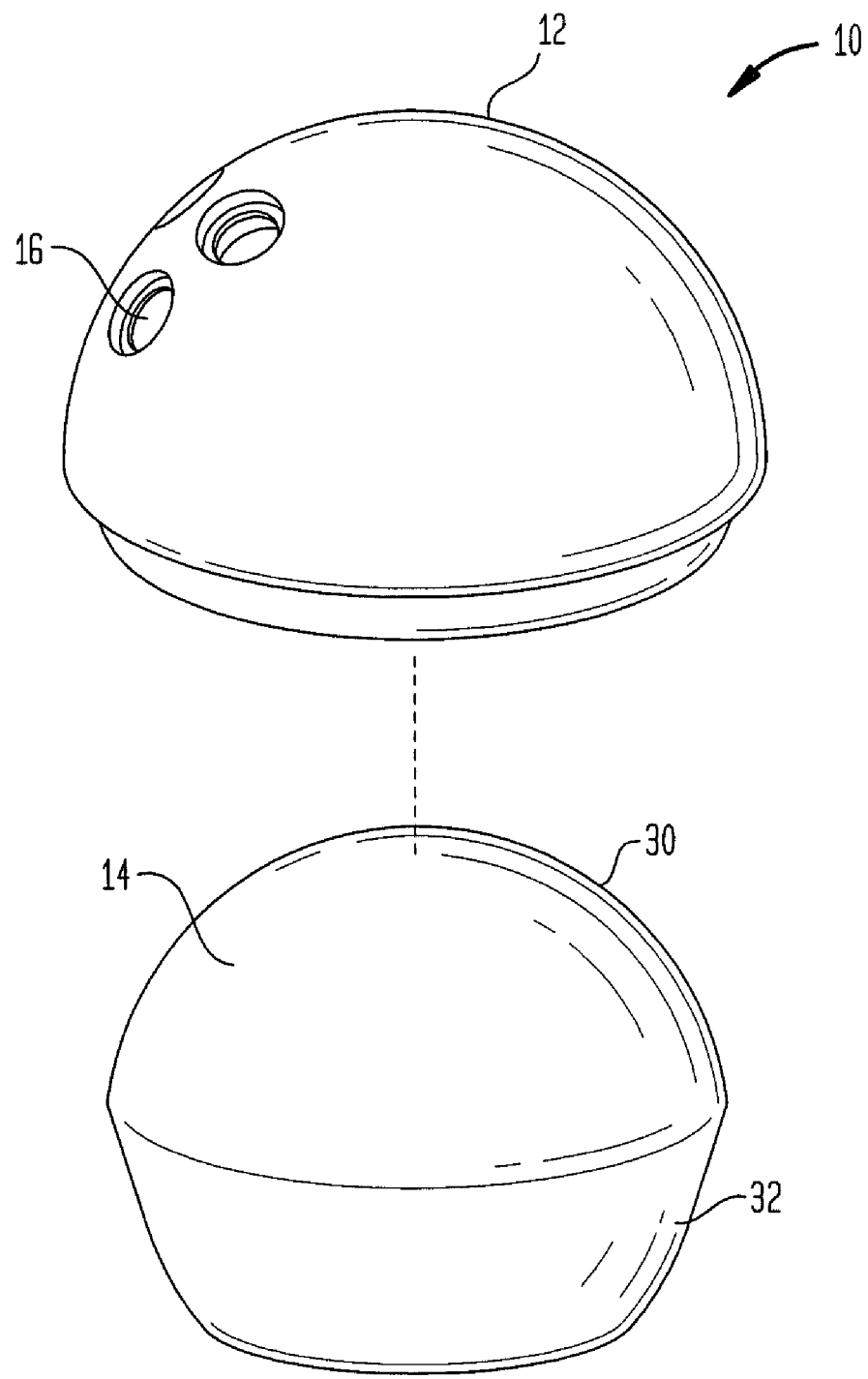
FIG. 1 is an exploded view of an acetabular cup with a housing with a rotatable bearing element mounted therein.
Figure 2:
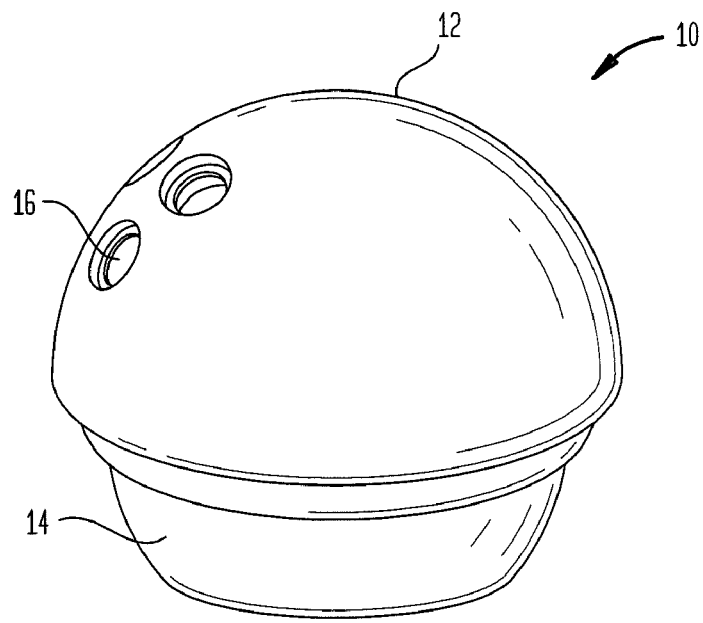
FIG. 2 shows the acetabular cup housing with rotatable bearing element of FIG. 1 assembled therein.
Figure 2A:
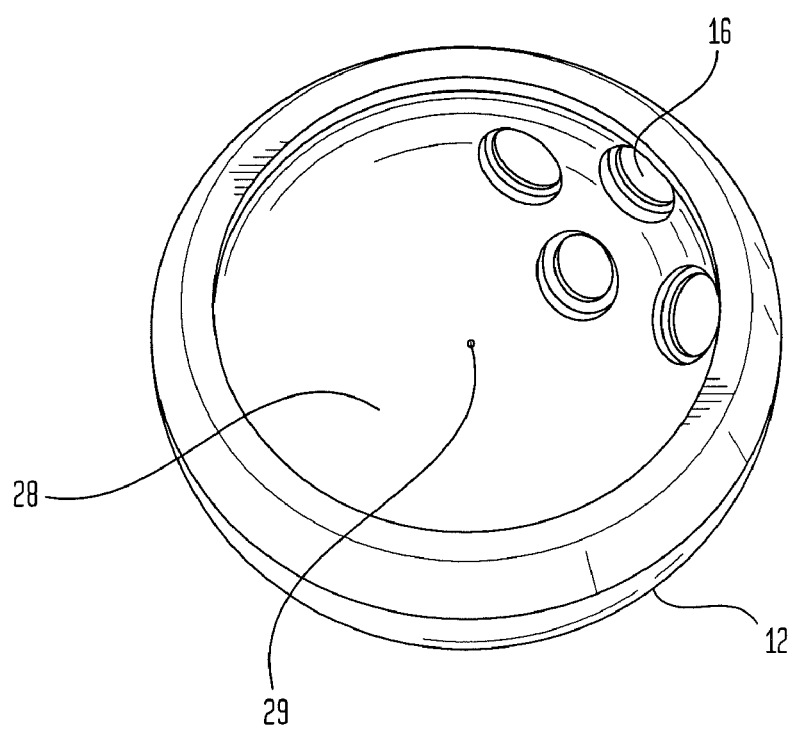
FIG. 2A is a bottom view of the housing of FIGS. 1 and 2.

Referring to FIG. 1 there is an exploded view of a two-part acetabular cup generally denoted as 10 with an outer housing 12 and a bearing element 14. Housing 12 is shown with bone screw holes 16 and bearing element 14 is shown having two part-spherical sections 30, 32. FIG. 2 shows the parts 12 and 14 assembled. FIG. 2A is a bottom view of the housing shown in FIG. 1 and has a circular opening 28 with a center 29. As shown in FIG. 2A, the housing 12 may include a plurality of through holes 16 for receiving screws (not shown) which hold the outer housing 12 to the acetabulum. The hole 16 could be eliminated if using a press-fit in the acetabulum. Bearing element 14 is one-piece and preferably made of ultra high molecular weight polyethylene but could also be made of a ceramic.

Figure 3:
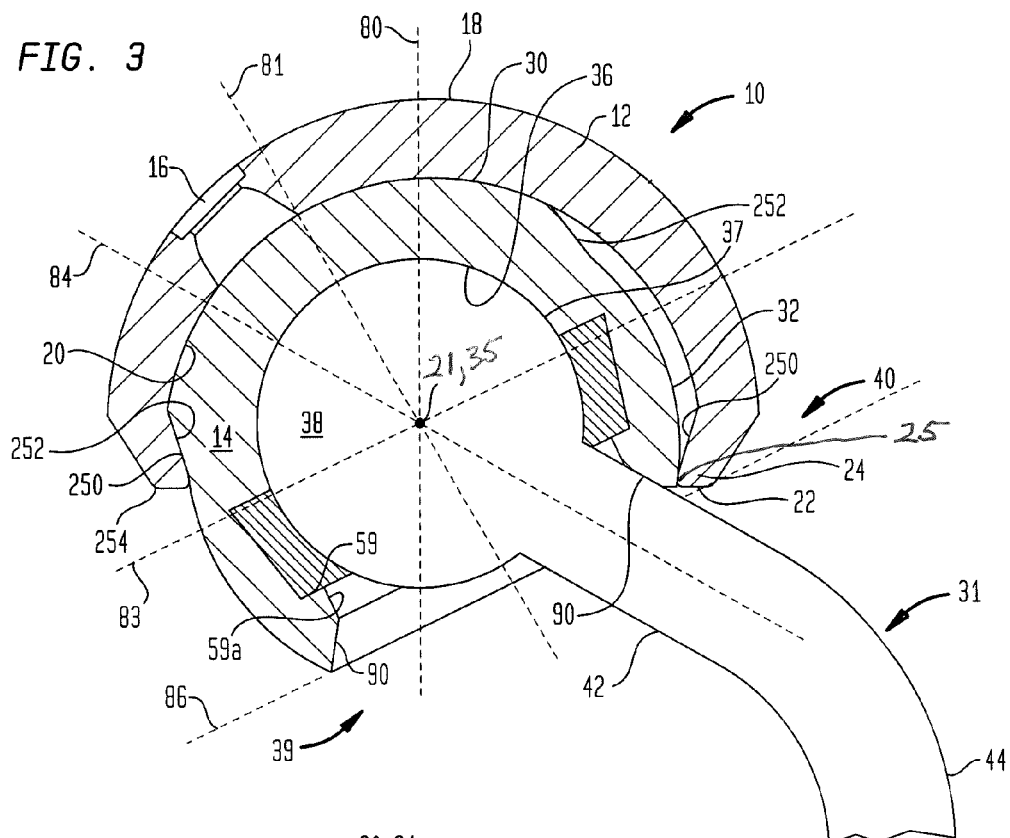
FIG. 3 is a cross-sectional view of the assembled cup of FIG. 2 including the head and neck of a femoral component mounted within the bearing element in a fully rotated position.

Referring to FIG. 3 there is shown a cross-sectional view of the assembled acetabular cup of FIG. 1 showing housing 12 having a part-spherical outer surface 18 and a part-spherical inner bearing surface 20. Surface 20 has a center 21. Housing includes a circumferential rim 22 including an area 24 extending radially inwardly and having a tip 25 defining a circular opening 28 with a center 29. Ramp 250 forms a shallow angle with respect to axis 80 and ramp 252 forms a shallow angle with respect to axis 81.

Figure 4:
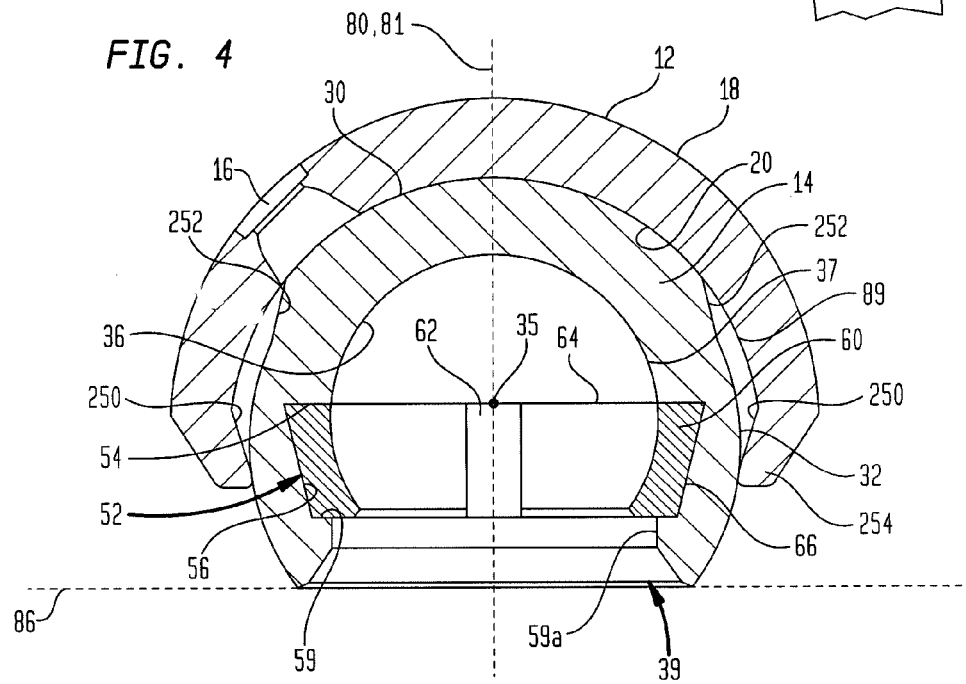
FIG. 4 is an assembled view of the acetabular cup and rotatable bearing element of FIGS. 1-3 in a centered position including a split locking ring.

Referring to FIGS. 3 and 4 there is shown an embodiment having oblique angled ramps 250 and 252. Ramp 250 is circumferentially formed on the inner surfaces of rim area 24 of the housing. Ramp or angled surface 252 is formed on the bearing element 14 between regions 30 and 32. The ramp angle can be as shallow as a few degrees (2-3 degrees) or can be greater for example between 10° and 30°. With a shallow ramp angle on both the bearing element and the housing the engagement between the surfaces gradually increases with increasing force until full engagement between the surfaces. The upwardly facing ramp surface 250 should be complimentary to the geometry of contact ramp surface 252 on bearing element 14. Bearing element 14 is shown mounted within opening 28 with a first part-spherical bearing surface region 30 engaging inner bearing surface 20 of housing 12. First part-spherical surface region 30 is capable of rotating on bearing surface region 20 in any direction and is shown rotated counter clockwise within housing 12 as a result of movement of the femoral component generally denoted as 31.

Bearing element 14 further includes a second part-spherical surface region 32 which extends from part-spherical bearing region 30 but has a smaller diameter and is spaced radially inwardly from surface 20. Thus there is no contact between surface 32 and surface 20. In a preferred embodiment the part-spherical bearing surfaces 30 and 32 are concentric and having the same center and are connected by a ramp (as illustrated in FIG. 3) or oblique angled surface 252 therebetween extending 360° around the outer surface of bearing element 14. In the embodiment shown in FIG. 3 the contact surface can be in the form of a ramp 250 at an oblique angle. It may also be possible to form the first part-spherical bearing surface 30 in two or more segments separated by, for example, narrow grooves thus interrupting the otherwise continuous contact surface 30.

Bearing element 14 includes an inner bearing surface 36 designed to receive an outer bearing surface 37 of a head 38 of a femoral component 31. Part-spherical bearing surface 36 has an open end 39 through which head 38 is inserted when the total joint is assembled. Femoral component head 38 is coupled to a neck 42 either as a one-piece construction or via a tapered male and female interconnection which is integrally formed with, or connected by a second male and female tapered interconnection, to an intramedullary stem 44. Such modular femoral component designs are well known. Stem 44 is intended to be received within a medullary canal of the femur although in certain oncological applications may form the entire proximal femur. In addition, femoral component 31 may be a trial femoral component and cup 10 could be a trial acetabular cup. As is typical, head engages and may rotate in any direction on part-spherical bearing surface 36 within bearing element 14.

Figure 5A:
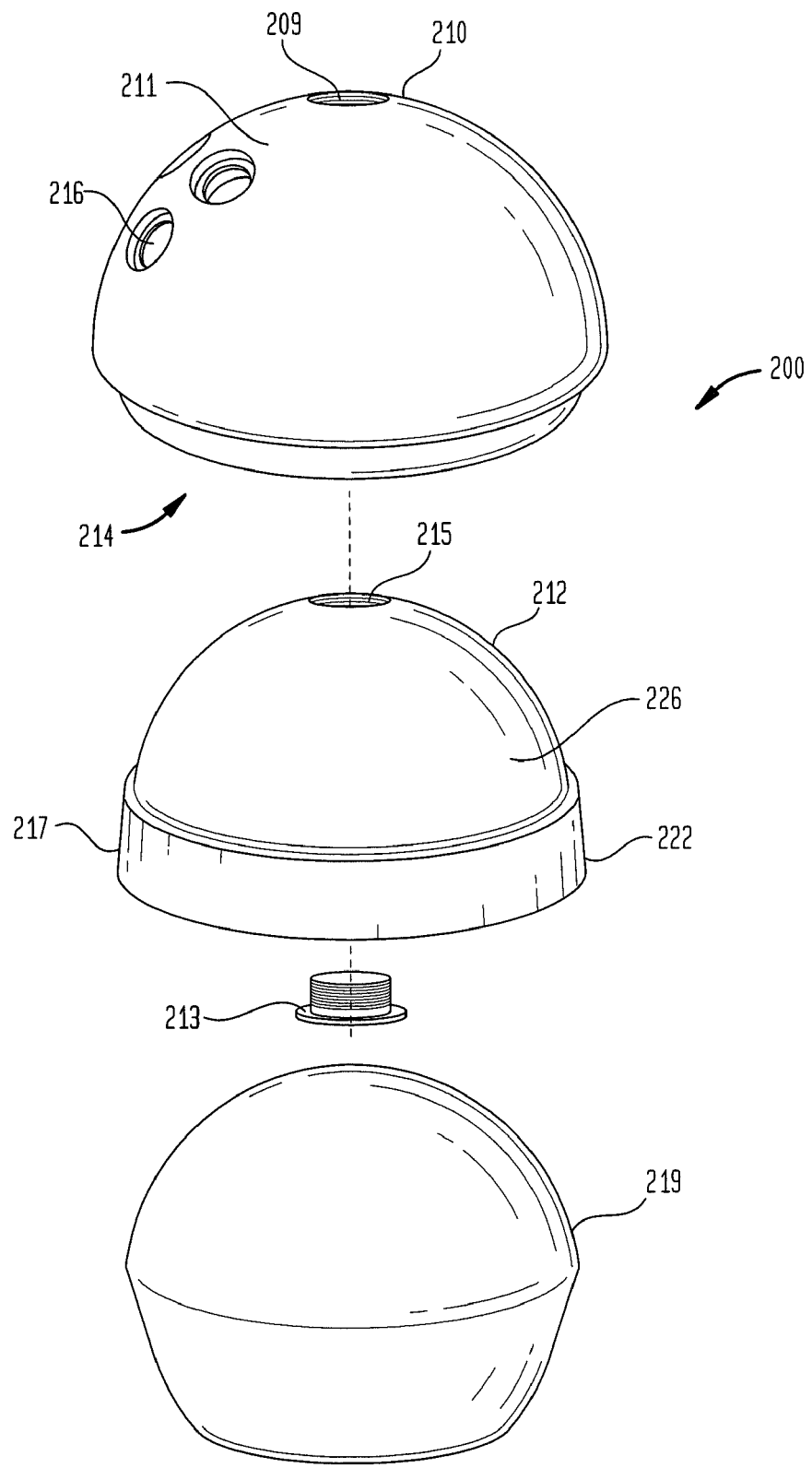
FIG. 5A shows an exploded view of an alternate embodiment with a two-piece backing comprising an outer shell and an inner housing fixed to the shell for receiving the bearing element.
Figure 5B:
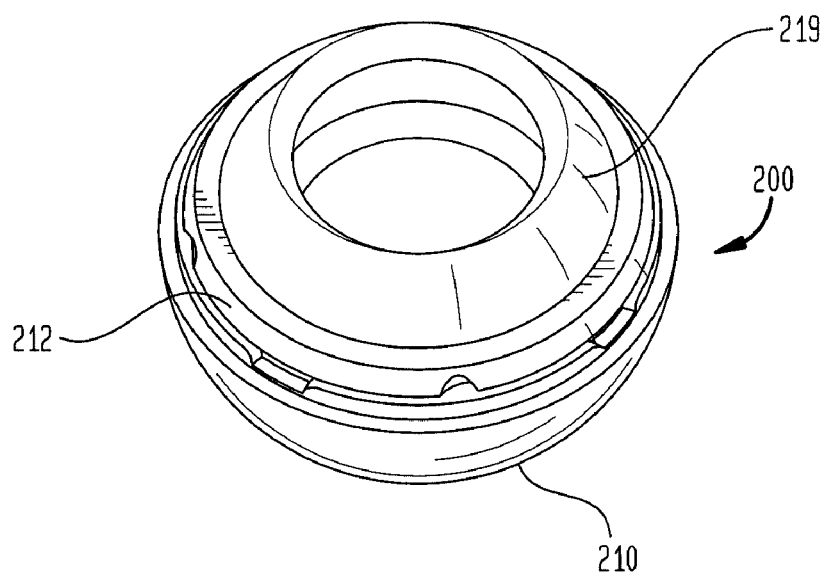
FIG. 5B is an assembled view of a three part cup having the shell, the housing and the bearing element of FIG. 5A.
Figure 5C:
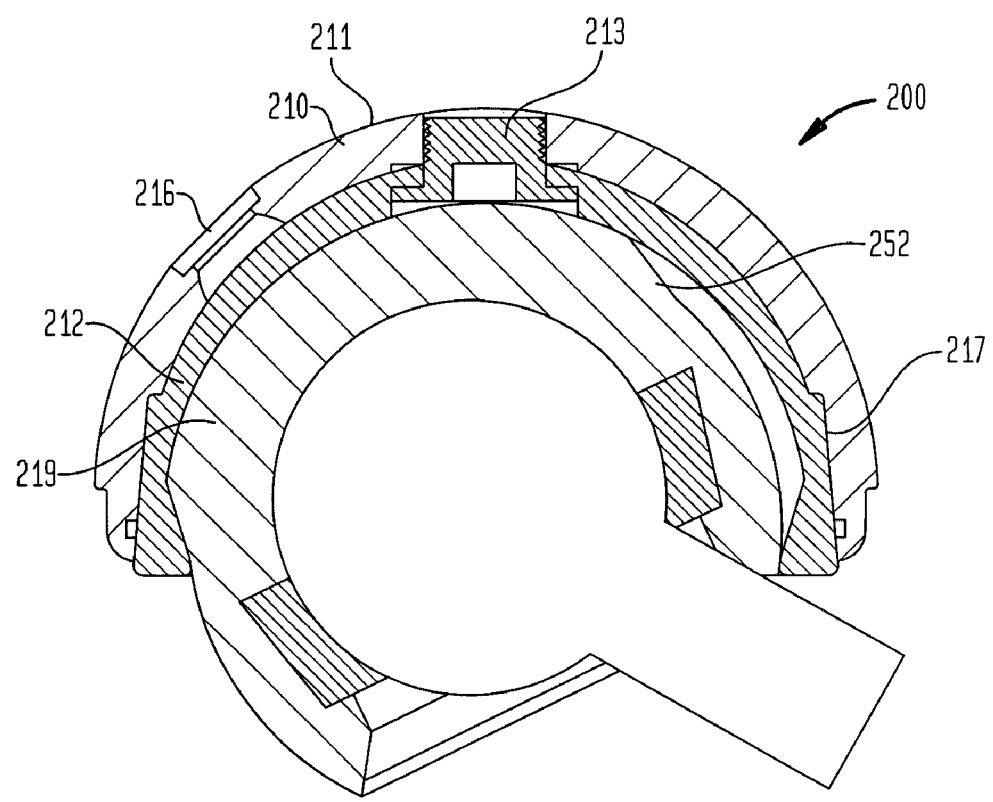
FIG. 5C is a cross-sectional view of the assembled alternate three piece assembly of FIGS. 5A and 5B.

Referring to FIGS. 5A-5C there is shown an alternate three-part acetabular cup with a rotatable bearing generally denoted as 200. Acetabular cup 200 includes an outer shell 210 which has an outer surface 211 for contacting the acetabulum. Shell 210 includes a threaded hole 209 at its pole. A separate housing 212 is mounted within shell 210 and held therein by a screw 213 inserted through a hole 215 in housing 212 into threaded hole 209 in shell 210 as well as interlocking tapers 217 adjacent the open end 214 of the shell and housing combination. A bearing insert or element 219 is mounted within housing 212. Housing 212 is identical to housing 12 with the exception of the bore 215 for receiving screw 213 and in the provision of an outer male tapered surface 217 around the rim 222. Bearing element 219 is an all respects identical to bearing element 14 discussed above.

The advantage of acetabular cup 200 is that heads of the screws through holes 216 of shell 210 have their heads covered by outer surface 226 of housing 212. Once assembled shell 210 and housing 212 cannot rotate with respect to one another and thus have their polar axis coaxial. As indicated above, screw holes 209, 215 are centered around the polar axis.

As shown in FIGS. 3 and 4, housing 12 has an axis 80 through a pole thereof (polar axis) which axis 80 is perpendicular to an equator through center 21 of the part-spherical housing inner surface 20 which equator is parallel to a plane across the opening in the acetabulum. In the preferred embodiment, the equatorial plane of the housing is also parallel to the plane defined by opening 28 of housing 12 and polar axis 80 extends through center 29 of opening 28.

Part-spherical bearing element surface portion 30 also has a polar axis 81 which is perpendicular to an equatorial plane 83 through center 35 of the bearing element 14 outer surfaces 30 and 32. The equatorial plane may be parallel to the plane 86 of open end 39 of bearing insert 14. Again, in the preferred embodiment, the polar axis 81 is also perpendicular to the plane of opening 39 when axis 80, 81 are aligned as shown in FIG. 4. The plane of the openings in the housing 12 and bearing element can be angled with respect to polar axis 80, 81 if the part-spherical surfaces extend at a greater angle on one side of the housing 12 and/or bearing 14 than another (see, for example, the acetabular cup shown in U.S. Pat. No. 5,108,445).

As shown in FIG. 3, part-spherical head 38 has an axis perpendicular to an equator through center 35. In the preferred embodiment, axis 84 is coaxial with the axis of the neck 42.

Referring to FIG. 4, there is shown bearing 14 partially inserted into housing 12 with axis 80 and 81 aligned. In the embodiment shown, the inner surface 36 of bearing element includes an outwardly extending recess 52 having upper end wall 54 extending laterally outwardly to an outer wall 56 of recess 52 which slopes downwardly and inwardly towards opening 39 through which head 38 is inserted. Outer wall 54 terminates in a lower end wall 59 which extends laterally inwardly and abuts a peripheral edge wall 59a forming part of opening 39 in the bearing element 14. Wall 59a is spaced inwardly of the plane 86 of opening 39 and is connected to plane 86 by beveled surface 90.

As shown in U.S. Pat. No. 4,798,610, the disclosure of which is incorporated herein by reference, a split ring 60, preferably constructed of ultra high molecular weight polyethylene similar to that used to construct the bearing element 14 has a split portion 62, rendering the ring 60 radially expandable and contractable. Ring 60 includes an upper end wall 64, a downwardly and inwardly sloping outer wall 66 of the same slope as outer wall 56 of recess 52 for mating engagement therewith. At assembly, head 38 is inserted axially into opening 39 in bearing element 14, past wall 59a and through ring 60, so that ring 60 will be raised axially upwardly to an upper position within recess 52 expanding ring 60. Once the equator or largest diameter of head 38 presses through ring 60 into engagement with part-spherical bearing surface 36 of bearing element 14, ring 60 contracts. When the ball contacts part-spherical inner surface 36, ring 60 contracts and slides downwardly along sloping walls 56, 66 capturing the head 38 in bearing element 14. Other methods of retaining the ball within the bearing element may be used such as that shown in U.S. Pat. No. 7,455,694 the disclosure of which is incorporated herein by reference.

Figure 6:
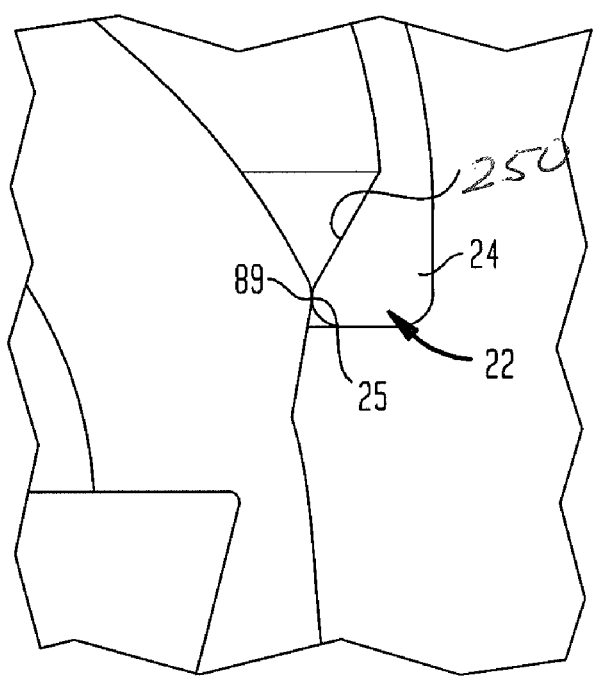
FIG. 6 shows an insertion clearance between a first part-spherical portion of the bearing element and the inwardly extending flange on a rim of a housing.
Figure 7:
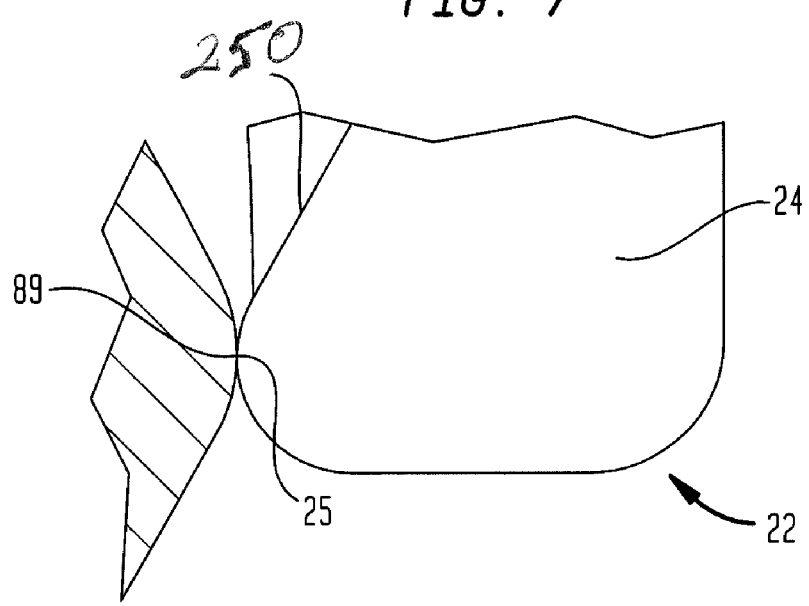
FIG. 7 shows a slight interference during insertion between the tip of the flange and an equatorial region of a second part-spherical outer surface of the bearing element.

Referring to FIGS. 6 and 7, there is shown details of the method for inserting a polyethylene bearing element 14 into housing 12 which method is the same in the two or three part designs shown in FIGS. 3 and 4 or 5A-5C respectively. The diameter of opening 28 formed by a tip 25 of area 24 is designed such that a tip 89 of tapered or ramp contact surface 252, which extends circumferentially around bearing element 14 between the first spherical portion 30 and the second spherical portion 32, has a diameter slightly less than the diameter of the opening to produce a very small clearance allowing insertion of bearing element 14 partially within housing 12. The largest diameter i.e. at the equator of second spherical part 32 has a diameter which produces a slight interference with the diameter of the opening so that during assembly a "snap" fit is produced just prior to insert 14 being fully inserted within housing 12.

In a preferred embodiment the first part-spherical surface region 30, the second part-spherical surface region of 32 and the part-spherical inner surface 36 are all concentric and thus have the same center 35 but different radii. Thus, axis 80, 81 through the center 35 perpendicular to the equator plane 83 of the bearing intersects the inner part-spherical surface 36 and the first part-spherical surface 30 at a pole of the spherical surfaces as described above.

In one embodiment of the present invention the first part-spherical surface extends to a latitude of about 40 to 45 degrees with respect to polar axis 81 with contact surface 34 extending at a similar angle between surfaces 30 and 32.

During use, bearing element 14 rotates within housing on surface 30 and head and neck 38, 42 rotates within the bearing element 14 on surface 36. When neck 42 makes contact with bearing element 14 it engages a beveled circumferential surface 90 which extends around opening 39 of bearing element 14. When the neck 42 engages surface 90 the bearing element 14 is rotated within housing 12 which rotation is limited by the engagement of contact surface 252 and upper surface 250 of rim area 24. At this point no relative rotation between the neck 42 of femoral component 40 is possible in this direction of rotation. Contact surface 252 is located at a latitude with respect to the pole 80 of housing 12 such that the rotation of bearing element 40 is stopped at a point which spaces the surface of neck 42 away from the tip 25 of flange 24. Thus, neck 42 always engages the ultra high molecular weight polyethylene bearing element 14 rather than the metal of housing 12. Preferably the start of contact surface 252 extends circumferentially around a latitude of 45° from the polar axis 81 of bearing element 14. The contact surface may start at any angle between surfaces 30 and 32 and extend inwardly at a shallow oblique angle. As discussed above, contact surfaces 250, 252 are angled at an oblique angle to axis 80 and have the ability to produce a less abrupt stop as would a steeper angle as the interference between the mating parts incrementally increases with each additional degree of rotational motion of the bearing element 14 relative to the housing 12.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic hip implant system comprising:
   a prosthetic femoral component having a stem portion, a neck portion coupled to the stem portion and a part-spherical head coupled to the neck portion;
   an acetabular component comprising:
   a housing, the housing having a part-spherical inner bearing surface having an open end with a circumferential rim portion, the rim portion having a circumferential radially inwardly angled ramp portion;
   a bearing element having a part-spherical first outer bearing surface region engaging the part-spherical inner bearing surface of the housing, the bearing element having a part-spherical inner surface region having an open end for receiving the head of the femoral component, the part-spherical first outer surface region of the bearing element extending about a central axis of the inner surface open end, the central axis intersecting a pole of the part-spherical outer surface region and a center of rotation of the part-spherical first outer surface region, the bearing element having a second part-spherical outer surface region extending from adjacent the open end towards the pole, the first outer surface region extending further from a center of rotation of the part-spherical inner surface of the bearing element than the second part-spherical surface region and an angled ramp portion engagable with the housing angled ramp portion formed between the first and second part-spherical outer surface region.

2. The prosthetic implant system as set forth in claim 1 wherein the bearing element part-spherical first outer surface region extends from the pole towards the open end to define an outer edge of the angled ramp portion extending between the part-spherical first surface and the second outer surface regions.

3. The prosthetic hip implant system as set forth in claim 2 wherein the bearing element and housing angled ramp portions extend 360 degrees around the part-spherical first outer surface region and the second outer surface region.

4. The prosthetic hip implant as set forth in claim 2 wherein the outer edge of the angled ramp portion is located on the bearing element intermediate the pole and an equator which extends through the center of rotation of the part-spherical first outer surface region and perpendicular to the central axis of the first part-spherical outer surface region.

5. The prosthetic hip implant system as set forth in claim 4 wherein the outer edge of the angled ramp portion is located at a position intermediate the pole and the equator such that upon rotation of the bearing element with respect to the housing the neck of the femoral component contacts the bearing element open end prior to the circumferential and radially inwardly angled ramp portion of the housing.

6. The prosthetic hip implant system as set forth in claim 5 wherein the circumferential contact surface extends around a latitude of 40° to 45° from the equator.

7. The prosthetic hip implant system as set forth in claim 5 wherein the circumferential and radially inwardly angled ramp portion of the housing rim portion has an inner diameter.

8. The prosthetic hip implant system as set forth in claim 7 wherein the outer diameter of second part-spherical outer surface region at the equator is inwardly deformable upon the interference to a diameter less than the inner diameter of the circumferential and radially inwardly angled ramp portion of the housing.

9. The prosthetic hip implant system as set forth in claim 1 wherein the housing is mounted within a shell contacting an acetabulum.

10. The prosthetic hip implant as set forth in claim 9 wherein the housing is mounted on the shell by a screw.

11. The prosthetic hip implant system as set forth in claim 1 wherein the bearing element has a center point which is the center of rotation of the first and second part-spherical outer surface regions and the part-spherical inner surface region.

12. The prosthetic hip implant system as set forth in claim 1 wherein the angled ramp portion forms an angle of less than 30° with the central axis.

13. A prosthetic hip implant system comprising:
    a prosthetic femoral component having a stem portion, a neck portion coupled to the stem portion and a part-spherical head coupled to the neck portion;
    an acetabular component comprising:
    a housing, the housing having a part-spherical inner bearing surface with an open end with a circumferential rim portion, the rim portion having a circumferential radially inwardly extending flange; and
    a bearing element having first and second part-spherical outer surfaces, the first part-spherical outer surface is rotatable on the housing inner bearing surface and is defined by a first radius extending from a center, the second part-spherical surface defined by a second radius from the center which is less than the first radius, an angled ramp portion formed between the first and second outer surfaces at an angle of 30° or less with respect to a polar axis of the bearing element through the center.

14. The prosthetic hip implant as set forth in claim 13 wherein a circumferential contact surface extends between an end of the first part-spherical outer surface and the second part-spherical outer surface.

15. The prosthetic hip implant system as set forth in claim 14 wherein the circumferential contact surface extends 360 degrees around the part-spherical first outer surface region and the second outer surface region.

16. The prosthetic hip implant system as set forth in claim 15 wherein the circumferential contact surface extends along a line forming an angle between 40° and 45° to a polar axis extending through the center and perpendicular to a plane across the housing open end.

17. The prosthetic implant system as set forth in claim 13 wherein the bearing element part-spherical first outer surface region extends from the pole towards the open end to define an outer edge of a circumferential contact surface extending between the part-spherical first surface and the second outer surface regions.

18. The prosthetic hip implant as set forth in claim 17 wherein the circumferential contact surface is located on the bearing element intermediate the pole and an equator which extends through the center of rotation of the part-spherical first outer surface region and perpendicular to the central axis of the first part-spherical outer surface region.

19. The prosthetic hip implant system as set forth in claim 18 wherein the circumferential contact surface is located at a position intermediate the pole and the equator such that upon rotation of the bearing element with respect to the housing the neck of the femoral component contacts the bearing element open end prior to the inwardly extending circumferential flange portion of the housing.

20. The prosthetic hip implant system as set forth in claim 19 wherein the inwardly extending circumferential flange of the housing rim portion has an inner diameter larger than a maximum outer diameter of the first part-spherical outer surface region of the bearing element to provide a clearance and less than an outer diameter at an equator of the second part-spherical outer surface region to produce an interference therebetween.

* * * * *